(12) United States Patent
Sharpless

(10) Patent No.: US 9,313,867 B2
(45) Date of Patent: Apr. 12, 2016

(54) IMAGING SYSTEM GANTRY

(71) Applicant: KONINKLIJKE PHILIPS N.V., Eindhoven (NL)

(72) Inventor: Ronald B. Sharpless, Cleveland, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 139 days.

(21) Appl. No.: 14/363,337

(22) PCT Filed: Dec. 7, 2012

(86) PCT No.: PCT/IB2012/057050
§ 371 (c)(1),
(2) Date: Jun. 6, 2014

(87) PCT Pub. No.: WO2013/093691
PCT Pub. Date: Jun. 27, 2013

(65) Prior Publication Data
US 2014/0321602 A1  Oct. 30, 2014

Related U.S. Application Data

(60) Provisional application No. 61/577,820, filed on Dec. 20, 2011.

(51) Int. Cl.
*A61B 6/00* (2006.01)
*H05G 1/04* (2006.01)
*A61B 6/03* (2006.01)
*F16C 27/04* (2006.01)
*F16C 35/077* (2006.01)
*F16C 27/00* (2006.01)
*G01N 23/04* (2006.01)

(52) U.S. Cl.
CPC ...... *H05G 1/04* (2013.01); *A61B 6/035* (2013.01); *F16C 27/00* (2013.01); *F16C 27/04* (2013.01); *F16C 35/077* (2013.01); *G01N 23/046* (2013.01); *F16C 2316/10* (2013.01)

(58) Field of Classification Search
CPC ......... H05G 1/04; G01N 23/046; F16C 27/00
USPC ...................................... 378/4–20, 193–197
See application file for complete search history.

(56) References Cited

U.S. PATENT DOCUMENTS 7,429,134 B2    9/2008  Brandenstein et al.
7,766,555 B2    8/2010  Kono et al.
(Continued)

FOREIGN PATENT DOCUMENTS

DE    102008026202 A1    12/2009
DE    102008064486 A1    7/2010
(Continued)

*Primary Examiner* — Courtney Thomas

(57) ABSTRACT

An imaging system (100) includes a stationary gantry (102), a rotating gantry (104) that rotates around an examination region about a z-axis, an annular support (106) that is statically affixed to the stationary gantry and that rotatably couples the rotating gantry to the stationary gantry, and a radial compliant ring (108) disposed between the annular support and the rotating gantry. In a variation, the imaging system also includes an axial compliant ring (112) disposed perpendicular to the radial compliant ring, statically affixed to the annular support and extending in part in a recess (206) of the rotating gantry.

19 Claims, 4 Drawing Sheets

(56) References Cited

U.S. PATENT DOCUMENTS

Figure 13:
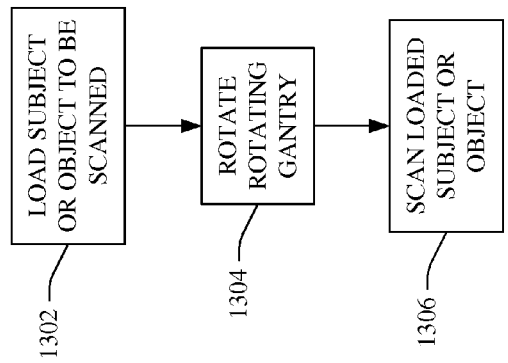

| | | | |
|---|---|---|---|
| 2008/0197303 A1* | 8/2008 | Aoi | A61N 5/1081 250/522.1 |
| 2009/0103845 A1 | 4/2009 | Meier et al. | |
| 2009/0154865 A1 | 6/2009 | Neubert et al. | |
| 2012/0027183 A1 | 2/2012 | Sharpless et al. | |

FOREIGN PATENT DOCUMENTS

| | | |
|---|---|---|
| EP | 1956257 A2 | 8/2008 |
| WO | 2008061076 A2 | 5/2008 |
| WO | 2009037261 A1 | 3/2009 |
| WO | 2011032301 A1 | 3/2011 |

* cited by examiner

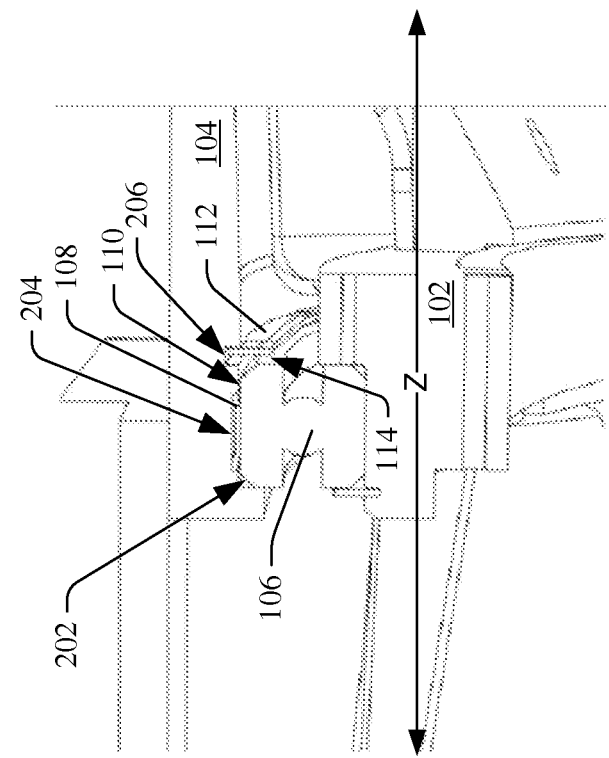
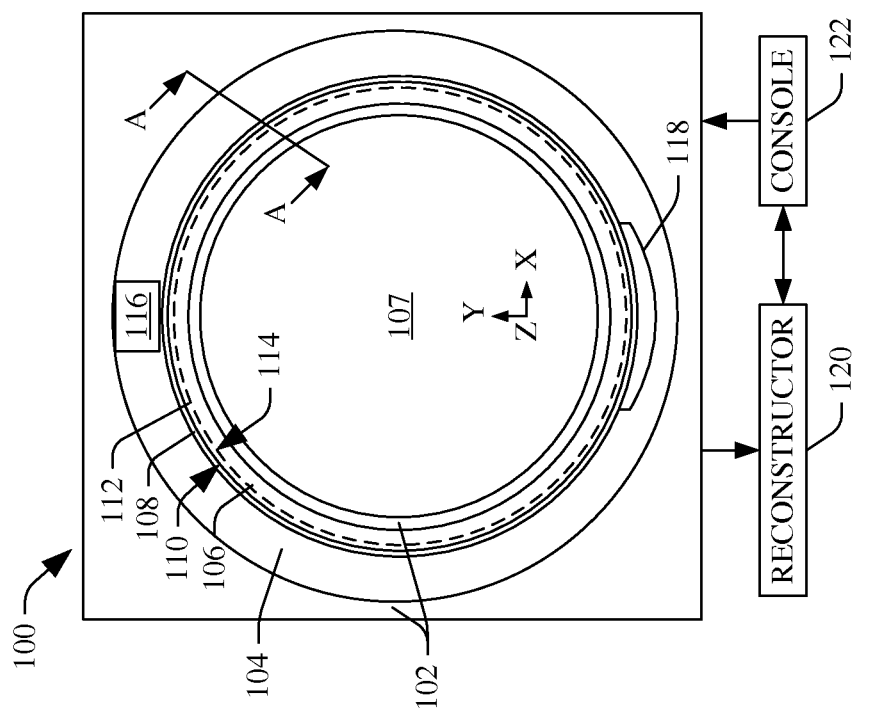
FIGURE 2
FIGURE 1

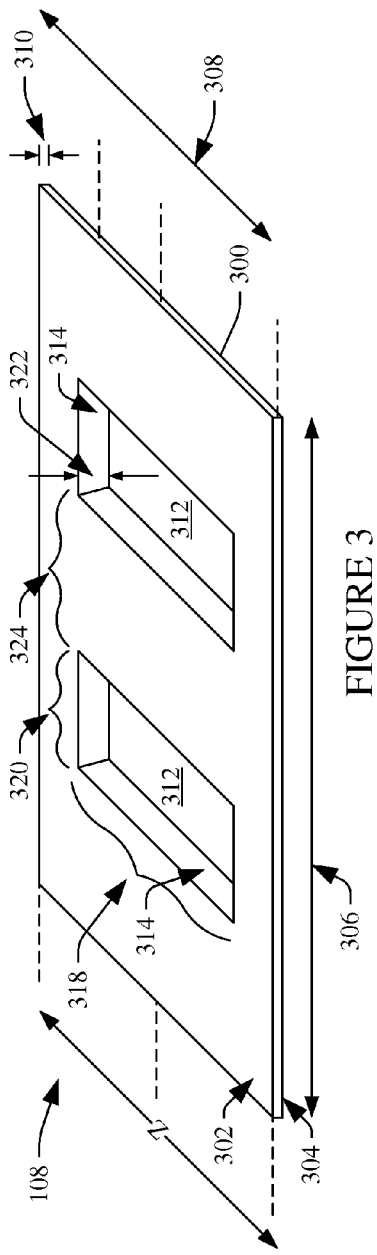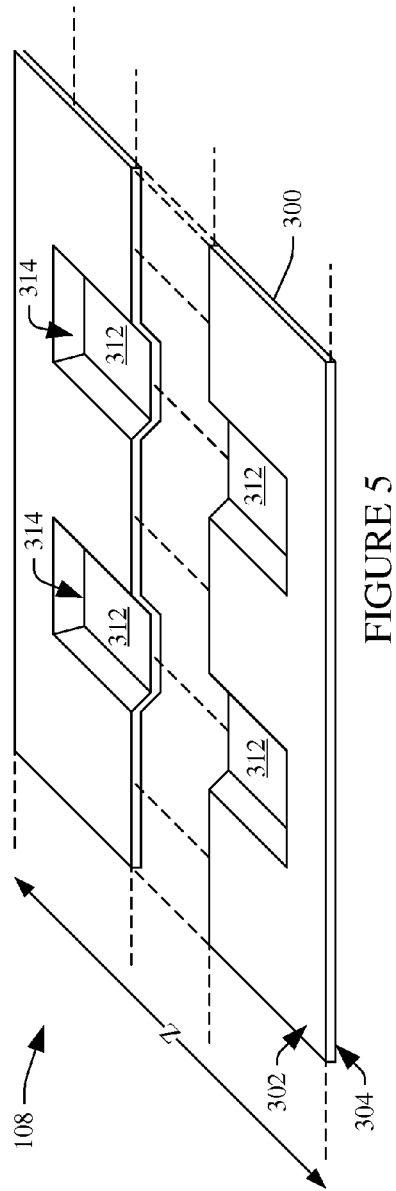

IMAGING SYSTEM GANTRY

CROSS REFERENCE TO RELATED APPLICATIONS

This application is a national filing of PCT application Ser. No. PCT/IB2012/057050, filed Dec. 7, 2012, published as WO 2013/093691 A1 on Jun. 27, 2013, which claims the benefit of U.S. provisional application Ser. No. 61/577,820 filed Dec. 20, 2011, which is incorporated herein by reference.

The following generally relates to an imaging system and more particularly to an imaging system gantry, and finds particular application with computed tomography (CT) imaging. However, it is also amenable to other imaging modalities.

A computed tomography (CT) scanner includes a stationary gantry and a rotating gantry, which is rotatably supported by the stationary gantry. The rotating gantry supports an x-ray tube. The stationary gantry and hence the x-ray tube rotate around an examination region about a z-axis. A detector array, located opposite the x-ray tube across the examination region detects radiation traversing the examination region.

Unfortunately, various forces (e.g., gravitational, centrifugal, etc.) acting on the rotating gantry tend to cause stresses that may decrease the lifetime and performance of various components, such as the bearing used to couple the rotating gantry. In addition, a relatively flexible bearing is often rigidly coupled to relatively stiff stationary and rotating gantry. As a result, raceway distortion may occur, which can introduce raceway stress when rotating the rotating gantry. The amount of such stress generally is proportional to the deformation and mounted stiffness. Furthermore, the mounting surface may vary in accuracy from scanner to scanner, which can lead to a wide variance in performance of the bearing.

Furthermore, rotating frame mass distribution imperfections cause a certain amount of static and dynamic rotor imbalances. Such imbalances can cause the rotating frame to wobble, which may vary the center of the field of view during a scan, which can degrade image quality. The degree of wobble is based on various factors such as the rotational speed of the rotating frame, the stiffness of the supporting structure, etc.

Aspects described herein address the above-referenced problems and others.

In one aspect, an imaging system includes a stationary gantry, a rotating gantry that rotates around an examination region about a z-axis, an annular support that is statically affixed to the stationary gantry and that rotatably couples the rotating gantry to the stationary gantry, and a radial compliance ring disposed between the annular support and the rotating gantry.

In another aspect, a method includes rotating a rotating gantry of an imaging system about a stationary gantry of the imaging system, wherein the rotating gantry is rotatably affixed to the stationary gantry via an annular support and a radial compliance ring, which resides between the rotating gantry and the annular support.

In another aspect, an imaging system gantry sub-system includes an annular support that statically affixes to a stationary gantry of the imaging system and that rotatably couples a rotating gantry to the stationary gantry, a radial compliance ring disposed between the annular support and the rotating gantry, wherein the rotating gantry rotates along the radial compliance ring, and an axial compliance ring, which is perpendicular to the radial compliance ring, and which is also disposed between the annular support and the rotating gantry.

The invention may take form in various components and arrangements of components, and in various steps and arrangements of steps. The drawings are only for purposes of illustrating the preferred embodiments and are not to be construed as limiting the invention.

FIG. 1 schematically illustrates an example imaging system, including a radial compliance ring and an optional axial compliance ring.

FIG. 2 schematically illustrates a cross-sectional view of the example imaging system, showing the radial compliance ring and the optional axial compliance ring.

FIG. 3 schematically illustrates a perspective view of the example radial compliance ring.

FIG. 4 schematically illustrates a side view of the example radial compliance ring.

FIG. 5 schematically illustrates the example radial compliance ring cut in half, showing the waves formed therein.

Figure 6:
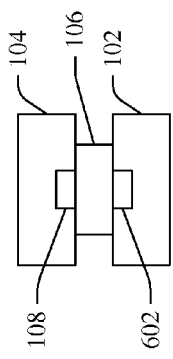

FIG. 6 schematically illustrates a variation in which a second radial compliance ring is affixed to the annular support between the annular support and the stationary gantry.

Figure 7:
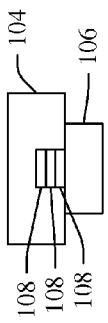

FIG. 7 schematically illustrates a variation in which a plurality of radial compliance rings is staked one on top of another.

Figure 8:
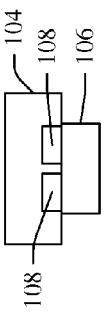

FIG. 8 schematically illustrates a variation in which a plurality of radial compliance rings is arrangement consecutively along the z-axis.

Figure 9:
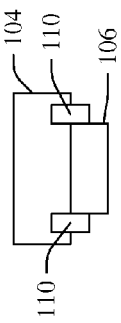

FIG. 9 schematically illustrates a variation including at least a second axial compliance ring.

Figure 10:
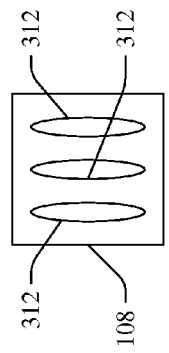

FIG. 10 schematically illustrates a radial and/or axial compliant ring with elliptical shaped waves.

Figure 11:
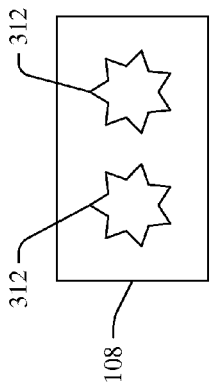

FIG. 11 schematically illustrates a radial and/or axial compliant ring with star shaped waves.

Figure 12:
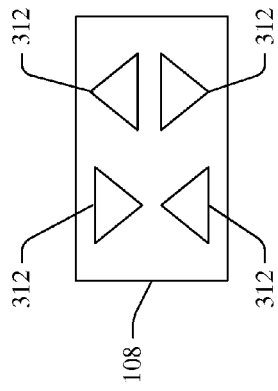

FIG. 12 schematically illustrates a radial and/or axial compliant ring with rows of waves, one on top of the other.

FIG. 13 illustrates an example method in accordance with the embodiments and/or variations described herein.

Figure 14:
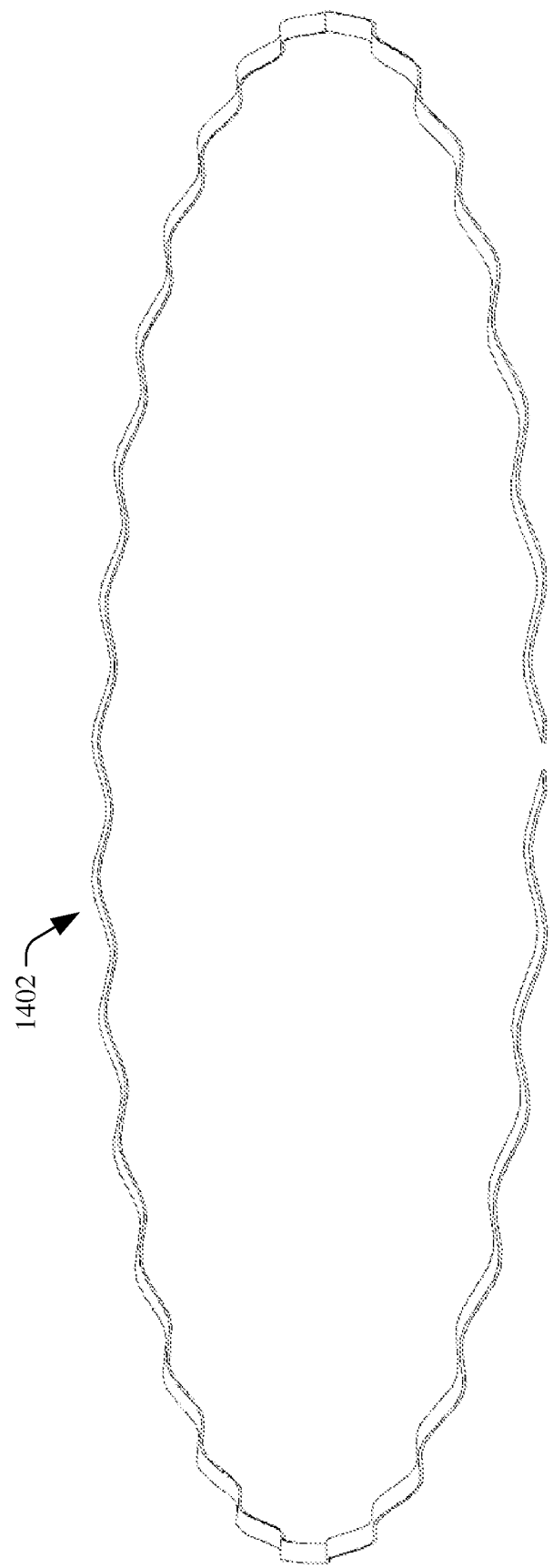

FIG. 14 schematically illustrates a non-limiting example of the axial compliance ring.

FIG. 1 illustrates an example imaging system 100, such as a computed tomography (CT) scanner. The imaging system 100 includes a generally stationary gantry 102 and a rotating gantry 104. The rotating gantry 104 is rotatably supported by the stationary gantry 102 through an annular support 106, such as a ball track and/or other bearing, and rotates along the annular support 106 around an examination region 107 about a z-axis. Where the system 100 is configured to tilt, the system 100 also includes a tilt frame (not shown).

At least one radial compliant ring 108 is disposed in connection with the annular support 106. As described in greater detail, in one instance, the at least one radial compliant ring 108 includes an elastic material, is pre-loaded and disposed between the annular support 106 and the rotating gantry 104, and circles a first outer surface 110 of the annular support 106, forming a ring around the annular support 106. An optional axial compliant ring 112 is also disposed in connection with the annular support 106.

As described in greater detail, in one instance, the optional axial compliant ring 112 includes an elastic material, is pre-loaded, and circles a second outer surface 114 of the annular support 106, which is perpendicular to the first outer surface 110 and the z-axis. The at least one radial compliant ring 108 and/or the optional axial compliant ring 112 can be closed or open rings, and/or composed of a single member or a plurality of individual segments.

Briefly turning to FIG. 2, a cross-sectional view of a sub-portion of the imaging system 100, along line A-A of FIG. 1, shows a non-limiting arrangement of the radial compliant ring 108 and the axial compliant ring 112 in connection with the annular support 106.

In FIG. 2, the rotating gantry 104 includes a first recess 202 in which a sub-portion of the annular support 106 protrudes within. The rotating gantry 104 also includes a second recess 204, which is located in the first recess 202. The annular support 106 is disposed in the first recess 202 such that the first surface 110 is adjacent to the second recess 204. The radial compliant ring 108 resides in the second recess 204 and is adjacent to the first surface 110. The rotating gantry 104 also includes a third recess 206, which is also in the first recess 202 and separated from the second recess 204, along the z-axis. The axial compliant ring 108 is affixed to the annular support 106 and protrudes into the third recess 206.

The rotating gantry 104 rotates along the radial and axial compliant rings 108 and 112. The radial compliant ring 108 rotates with the rotating gantry 104, and the axial compliant ring 112 remains stationary. A lubricant, such as a gel and/or liquid lubricant, can be used in connection with one or both of the radial and/or axial compliance rings 108 or 112. The optional lubricant may reduce friction in connection with the radial and/or axial rings 108 or 112.

Generally, the rings 108 and/or 112 decouple the rotating and stationary gantries 104 and 102. For example, the radial compliant ring 108 absorbs radial machining tolerances and/or operating radial distortions of the annular support 106 and/or stationary gantry 102 and/or compensates for thermal differentials and/or provides sufficient stiffness during operation. The overall radial stiffness of the radial compliant ring 108 can be sized such that the rotating gantry 104 static imbalance forces cause trivial displacements of the rotation center. The axial compliant ring 112 absorbs axial machining tolerances and operating axial distortions of the annular support 106 and/or stationary gantry 102 and/or compensates for thermal differentials and/or dynamic imbalance operating loads of the rotating gantry 104 and/or rotating gantry 104 offset load.

The annular support 106 and the stationary gantry 102 can be variously coupled. In this embodiment, the annular support 106 is affixed to the stationary gantry 104 via an adhesive such as a glue, tape, etc. In another embodiment, the annular support 106 and the stationary gantry 104 are bolted together via one or more nut and bolt pairs. In yet another embodiment, the annular support 106 is coupled to the stationary gantry 104 via one or more screws. Other fastening mechanisms are also contemplated herein.

Returning to FIG. 1, a radiation source 116, such as an x-ray tube, is rotatably supported by the rotating gantry 104, rotates with the rotating gantry 104, and emits radiation that traverses the examination region 107. A one or two dimensional radiation sensitive detector array 118 subtends an angular arc opposite the radiation source 116 across the examination region 108. The detector array 118 detects radiation traversing the examination region 107 and generates projection data indicative thereof.

A reconstructor 120 reconstructs the projection data and generates image data indicative thereof. The console 122 includes a human readable output device such as a monitor or display and an input device such as a keyboard, mouse, etc. Software resident on the console 122 allows the operator to interact with and/or operate the scanner 100. A general-purpose computing system or computer serves as an operator console 122. A subject support (not shown for clarity), such as a couch, supports the subject in the examination region 107.

FIGS. 3, 4 and 5 schematically illustrate an example of a sub-portion of the radial compliant ring 108. The axial compliant ring 112 is similarly structured. FIG. 3 shows a perspective view, FIG. 4 shows a side view, and FIG. 5, for explanatory purposes, shows the sub-portion split down the center along an axis transverse to the z-axis.

As noted above, the radial compliant ring 108 includes an elastic material. In this embodiment, the radial compliant ring 108 is a metal strip 300. Other elastic materials are also contemplated herein. The metal strip 300 includes first and second opposing major surfaces 302 and 304 and a non-zero length 306 (which is long enough to form a closed ring around the examination region 107), width 308 and thickness 310.

The metal strip has a series of waves 312, which form recesses 314 in the first surface 302 and protrusions 316 out of the second surface 304. The waves 312 can vary in number (e.g., from a few to many hundreds) and have non-zero lengths 318, widths 320 and heights 322, and are separated from each other by non-zero distances 324. The waves 312 provide a minimum radial stiffness that compensates for static imbalance along with a tolerable distortion range to accommodate tolerance build-up and operational distortions.

The waves 312 are pre-loaded with force (e.g., 50 lbs, 200 lbs, etc.), which may provide support through the operational temperature range of the imaging system (allowing for local thermal expansion and/or contraction differentials) and improve bearing torque transfer. The number and/or size of the waves 312 provide sufficient stiffness, tolerance compliance, torque, axial friction, and/or long fatigue life. This pre-load may also provide a primary axial retention via friction.

The tolerance range can be extended by increasing the wave height 314 and/or reducing the material thickness 310 and/or including at least a second radial compliant ring 108 in series. Stiffness can be increased by stacking radial compliant rings 108 one on another in parallel, and/or reducing the wave height 322 and/or increasing the material thickness 310.

Structurally, the axial compliant ring 110 is substantially similar to the radial compliant ring 108, and pre-loading can be such that predictable loads of rotating gantry center of gravity offset torque combined with the worst case rotating gantry 104 dynamic imbalance and tilt axial loads are mitigated. The preload makes the retention act as a rigid device. The stiffness can be made low while still providing high levels of safety and stability.

The axial compliant ring 110 waves 312 are sized such that fatigue life is appropriate for the axial tolerance capabilities along with the predictable operational axial deflections. Similar to the radial compliant ring 108, the axial operational deflections can be estimated.

Variations are contemplated.

FIG. 6 schematically illustrates a variation in which a second radial compliant ring 602 is affixed to the annular support 106 between the annular support 106 and the stationary gantry 102. Unlike the radial compliant ring 108 between the annular support 106 and the rotating gantry 104, the second radial compliant ring 602 does not rotate.

FIG. 7 schematically illustrates a variation in which N (where N is an integer equal to or greater than two) radial compliant rings 108 are staked one on top of another. As discussed above, this may increase stiffness.

FIG. 8 schematically illustrates a variation in which M (where M is an integer equal to or greater than two) radial compliant rings 108 are arranged next to each other, sequentially along the z-axis.

FIG. 9 schematically illustrates a variation at least a second axial compliant ring is located on a side of the annular support opposing the side the other axial compliant ring is attached to.

Other configurations, including a combination of one or more of the configurations shown in FIGS. 2-9, are also contemplated herein.

FIG. 10 schematically illustrates a radial compliant ring 108 with elliptical shaped waves 312.

FIG. 11 schematically illustrates a radial compliant ring 108 with star shaped waves.

FIG. 12 schematically illustrates a radial compliant ring 108 with two rows of waves, one on top of the other.

Other shapes of the wavers 312 are also contemplated herein. In addition, a radial compliant ring 108 may include two or more different shaped waves 312.

FIG. 13 illustrate an example method.

It is to be appreciated that the ordering of the acts in the methods described herein is not limiting. As such, other orderings are contemplated herein. In addition, one or more acts may be omitted and/or one or more additional acts may be included.

At 1302, an object or subject is loaded in the examination region 107 of the imaging system 100 via a subject support.

At 1304, the rotating gantry 104 of the imaging system 100 is rotated relative to the stationary gantry 102. As described herein, the rotating gantry 104 rotates via the annular support 106 with the radial compliant ring 108 disposed between the annular support 106 and the rotating gantry 104.

At 1306, the imaging system 100 is used to scan a subject for object.

FIG. 14 illustrates a non-limiting example of the axial compliant ring 112. In this example, the axial compliant ring 112 includes a series of continuous waves 1402. Similarly to the radial compliant ring 108, the illustrated width and/or thickness of the axial compliant ring 112 and/or the illustrated height and/or number of the waves 1402 are provided for explanatory purposes and is not limiting. As described above, the axial compliant ring 112 can be pre-loaded such that predictable loads of rotating gantry center of gravity offset torque combined with the worst case rotating gantry 104 dynamic imbalance and tilt axial loads are mitigated, and the preload makes the retention act as a rigid device. Note that the radial compliant ring 108 may likewise include a series of continuous waves.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An imaging system, comprising:
   a stationary gantry;
   a rotating gantry that rotates around an examination region about a z-axis, the rotating gantry, including:
   a first recess; and
   a second recess located in the first recess;
   an annular support that is statically affixed to the stationary gantry and that rotatably couples the rotating gantry to the stationary gantry, wherein a sub-portion of the annular support protrudes in the first recess and a first surface of the sub-portion is adjacent to the second recess; and
   a radial compliant ring disposed between the annular support and the rotating gantry in the second recess, adjacent to the first surface of the sub-portion of the annular support.

2. The imaging system of claim 1, wherein the rotating gantry rotates along radial compliant ring.

3. The imaging system of claim 1, the radial compliant ring, comprising: an elastic material.

4. The imaging system of claim 1, the radial compliant ring, comprising:
   a metal strip having first and second major surfaces and including a plurality of waves, which form recesses on the first major surface and protrusion on the second major surface.

5. The imaging system of claim 4, wherein the radial compliant ring is pre-loaded between the annular support and the rotating gantry such that it behaves as a spring therein.

6. The imaging system of claim 1, further comprising:
   at least a second radial compliant ring stationarily disposed between the annular support and the stationary gantry.

7. The imaging system claim 1, wherein the radial compliant ring is a closed ring.

8. The imaging system of claim 1, wherein the radial compliant ring is an open ring.

9. The imaging system of claim 1, wherein the radial compliant ring rotates with the rotating gantry.

10. The imaging system of claim 1, wherein the plurality of waves provide a minimum radial stiffness that compensates for at least one a static imbalance, tolerance build-up, and operational distortions of the stationary gantry.

11. The imagine system of claim 1, wherein a pre-loading of the radial compliant ring provide support through an operational temperature range of the imaging system, allow for local thermal expansion and/or contraction differentials.

12. The imaging system of claim 1, further comprising:
   an axial compliant ring disposed perpendicular to the radial compliant ring, statically affixed to the annular support and extending in part in the second recess of the rotating gantry.

13. The imaging system of claim 12, wherein the axial compliant ring is pre-loaded such that at least one of predictable loads of the rotating gantry center of gravity offset torque, the rotating gantry dynamic imbalance, and tilt axial loads are mitigated.

14. A method, comprising:
   rotating a rotating gantry of an imaging system about a stationary gantry the imaging system, wherein the rotating gantry is rotatably affixed to the stationary gantry via an annular support and a radial compliant ring, which resides between the rotating gantry and the annular support in a first recess located in a second recess in the rotating gantry and adjacent to a surface of the annular support which is located in the first recess.

15. The method of claim 14, wherein the radial compliant ring is pre-loaded, thereby acing as a spring between the rotating gantry and the annular support.

16. The method of claim 15, wherein the pre-loading provides primary axial retention through friction.

17. The method of claim 14, wherein the rotating gantry is rotatably affixed to the stationary gantry via an axial compliant ring, which is perpendicular to the radial support ring and statically affixed to the annular support, and which extends into a recess of the rotating gantry.

18. The method of claim 17, wherein the axial compliant ring is pre-loaded, thereby acting as a second spring between the rotating gantry and the annular support.

19. An imaging system gantry sub-system, comprising:
   an annular support that statically affixes to a stationary gantry of the imaging system and that rotatably couples a rotating gantry to the stationary gantry;
   a radial compliant ring disposed between the annular support and the rotating gantry in a recess in the rotating gantry and adjacent to a surface of the annular support, wherein the rotating gantry rotates along the radial compliant ring.

\* \* \* \* \*